US012625282B2

(12) United States Patent
Shaw et al.

(10) Patent No.: US 12,625,282 B2
(45) Date of Patent: May 12, 2026

(54) IN-SITU BETA-PARTICLE DETECTOR FOR HIGH RESOLUTION 234TH EXPORT MEASUREMENTS

(71) Applicant: UNIVERSITY OF SOUTH CAROLINA, Columbia, SC (US)

(72) Inventors: Timothy J. Shaw, Columbia, SC (US); Michael L. Myrick, Columbia, SC (US)

(73) Assignee: UNIVERSITY OF SOUTH CAROLINA, Columbia, SC (US)

( * ) Notice: Subject to any disclaimer, the term of this patent is extended or adjusted under 35 U.S.C. 154(b) by 189 days.

(21) Appl. No.: 18/667,350

(22) Filed: May 17, 2024

(65) Prior Publication Data

US 2024/0402363 A1 Dec. 5, 2024

Related U.S. Application Data

(60) Provisional application No. 63/504,833, filed on May 30, 2023.

(51) Int. Cl.
| | |
|---|---|
| *G01T 1/178* | (2006.01) |
| *G01N 1/10* | (2006.01) |
| *G01N 33/18* | (2006.01) |
| *G01T 1/203* | (2006.01) |
| *G01T 1/24* | (2006.01) |

(52) U.S. Cl.
CPC .............. *G01T 1/178* (2013.01); *G01N 1/10* (2013.01); *G01N 33/18* (2013.01); *G01T 1/203* (2013.01); *G01T 1/248* (2013.01); *G01N 2001/1031* (2013.01)

(58) Field of Classification Search
None
See application file for complete search history.

(56) References Cited

U.S. PATENT DOCUMENTS

2017/0045628 A1* 2/2017 Buesseler ............... G01T 1/178

OTHER PUBLICATIONS

Alldredge et al. "Mass aggregation of diatom blooms—insights from a mesocosm study". Deep-Sea Res. II 42: 9-27(1995). doi: 10.1016/0967-0645(95)00002-8.
Armstrong et al. "Settling velocity spectra and the ballast ratio hypothesis". *Deep-Sea Res.II_*56:1470-1478(2009). doi: 10.1016/j.dsr2.2008.11.032.
Baldwin et al. "Particulate matter fluxes into the benthic boundary layer at a long time-series station in the abyssal NE Pacific: composition and fluxes". *Deep-Sea Res. II* 45:643-665(1998). doi: 10.1016/S0967-0645(97)00097-0.

(Continued)

*Primary Examiner* — Edwin C Gunberg
(74) *Attorney, Agent, or Firm* — DORITY & MANNING, P.A.

(57) ABSTRACT

A sea going instrument is used to measure the $^{234}$Th activity on settling particles in the ocean as an indicator of carbon sequestration as export from the surface ocean. The instrumentation can be adapted to multiple sampling platforms with the goal of providing high temporal resolution $^{234}$Th flux measurements at multiple locations and depths in the ocean. This proxy of mass flux is used to complement other in situ sensors to provide high resolution data for features such as Chlorophyll-a concentration (Chla), accessory pigments, and PIC normalized to mass flux.

34 Claims, 3 Drawing Sheets

(56)                    References Cited

OTHER PUBLICATIONS

Bishop et al. "Autonomous observations of the ocean biological carbon pump". Oceanography 22(2):182-193 (2009), doi:10.5670/oceanog.2009.48.

Bishop et al. "Robotic observations of high wintertime carbon export in California coastal waters". Biogeosciences Discuss(2016). doi:10.5194/bg-2016-62.

Blue et al. "Calculation of Minimal Detectable Activity for Scintillation Detection Systems". J. Nuclear Med. Tech. 15(1): 5-7(1987).

Buesseler et al. "An assessment of particulate organic carbon to thorium-234 ratios in the ocean and their impact on the application of $^{234}$Th as a POC flux proxy. Mar. Chem. 100: 213-233(2006)". doi: 10.1016/j.marchem.2005.10.013.

Buesseler et al. High-resolution spatial and temporal measurements of particulate organic carbon flux using thorium-234 in the northeast Pacific Ocean during the EXport Processes in the Ocean from RemoTe Sensing field campaign. Elementa: Science of the Anthropocene 8 (1): 030(2020). doi: 10.1525/elementa.2020.030.

Buesseler et al. Shedding light on processes that control particle export and flux attenuation in the twilight zone of the open ocean. Limnol. Oceanogr. 54(4), 1210-1232(2009). doi:10_4319/10.2009 54.4.1210.

Chenillat et al. Biogeochemical properties of eddies in the California Current System. Geophys. Res Lett 43(2016): doi: 10.1002/2016GL068945.

Chu et al. "WWW Table of Radioactive Isotopes", database version Feb. 28, 1999 (1999)from URL http://nucleardata.nuclear.lu.se/nucleardata/toi/.

Formaggio et al. "Backgrounds to sensitive experiments underground. Ann. Rev. Nucl. Part. Sci. 54: 361-412"(2004). doi: 10.1146/annurev.nucl.54.070103.181248.

G. Heusser "Low-Radioactivity Background Techniques", Ann. Rev. Nuclear Particle Science 45, 543-590(1995). doi: 10.1146/annurev.ns.45.120195.002551.

Giering et al. Reconciliation of the carbon budget in the ocean's twilight zone. Nature, 507(7493), 480-483(2014). doi.org/10.1038/nature13123.

Henson et al. "Drivers of Carbon Export Efficiency in the Global Ocean". Global Biogeochem Cycles. 33(7):891-903(2019). doi:10.1029/2018GB006158.

Hiroyuki K.M. Tanaka "Muometric positioning system (μPS) with cosmic muons as a new underwater and underground positioning technique". Sci Rep 10, 18896(2020) . doi: 10.1038/s41598-020-75843-7.

Ken O Buesseler "The decoupling of production and particulate export in the surface ocean". Global Biogeochem. Cycles, 12: 297-310(1998).

Kwon et al. "The impact of remineralization depth on the air-sea carbon balance", Nat. Geosci. 2(9):630-635(2009). doi: 10.1038/NGEO612.

Laws et al. "Temperature effects on export production in the open ocean". Global Biogeochem. Cycles, 14( 4), 1231-1246,(2000) doi: 10.1029/1999GB001229.

Mcgill et al. "Sedimentation event sensor: New ocean instrument for in situ imaging and fluorometry of sinking particulate matter". Limnol. Oceanogr. Methods. (2016) doi: 10.1002/lom3.10131.

Moran et al. "Does 234Th/238U Disequilibrium Provide an Accurate Record of the Export Flux of Particulate Organic Carbon from the Upper Ocean?" Limnol. Oceanogr. 48(3), 1018-1029.(2003) http://www.jstor.org/stable/3096628.

Passow et al. "Accumulation of mineral ballast on organic aggregates". Global Biogeochem. Cycles 20, GB1013(2006), doi: 10.1029/2005GB002579.

Riley et al. "The relative contribution of fast and slow sinking particles to ocean carbon export". Global Biogeochemical Cycles, 26: GB1026(2012), doi: 10.1029/2011GB004085.

Savoye et al. "Th-234 sorption and export models in the water column: A review". Mar. Chem. 100: 234-249. (2006) doi: 10.1016/j.marchem.2005.10.014.

Shaw et al. "Model study of organic carbon attenuation and oxygen mass transfer in persistent aggregate layers in the deep sea". Deep Sea Res. II 173. 104760 (2020). doi:10.1016/j.dsr2.2020.104760.

Shaw et al. "Scavenging of ex$^{234}$Th, ex$^{230}$Th, and ex$^{210}$Pb by particulate matter in the deep waters of the California continental margin". Deep Sea Res. II 45: 763-779(1998). doi: 10.1016/S0967-0645(97)00101-X.

Sherman et al. "Lagrangian sediment traps for sampling at discrete depths beneath free-drifting icebergs". Deep Sea Res. II 58, 1327-1335(2011). doi: 10.1016/j.dsr2.2010.11.008.

Smith et al. "Deep ocean communities impacted by changing climate over 24 y in the abyssal northeast Pacific Ocean". Proc. Natl. Acad. Sci. USA. 110: 19838-19841(2013). doi: 10.1073/pnas.1315447110.

Smith et al. "Episodic organic carbon fluxes from surface ocean to abyssal depths during long-term monitoring in NE Pacific". Proc. Nat. Acad. Sci. 115. 201814559(2018). doi: 10.1073/pnas.1814559115.

Stukel et al. "Mesoscale ocean fronts enhance carbon export due to gravitational sinking and subduction". Proc. Natl. Acad. Sci. USA. 114:1252-1257(2017) doi: 10.1073/pnas.1609435114.

Van Der Loeff "A review of present techniques and methodological advances in analyzing 234Th in aquatic systems". Mar. Chem. 100:190-212(2006). doi: 10.1016/j.marchem.2005.10.012.

Virissimo et al. Influence of seasonal Variability in flux attenuation on global organic carbon fluxes and nutrient distributions. Global Biogeochemical Cycles, 36, e2021GB007101(2022). doi:10.1029/2021GB007101.

Waples et al. "Measuring low concentrations of $^{234}$Th in water and sediment". Mar. Chem. 80:265-281(2003). doi: 10.1016/S0304-4203(02)00118-4.

* cited by examiner

| Sample Resolution for 10% detector efficiency | Min Det dpm 150 cpm bkg | Min Det dpm 25 cpm bkg |
|---|---|---|
| 8 hours | 13 | 5 |
| 24 hours | 7.5 | 3 |

| Example Trap Comparison | Minimum dpm in an LST trap (0.1 m$^2$) | Minimum DPM in an SES trap (0.5 m$^2$) |
|---|---|---|
| Eq Pacific 100m, Measured Range in dpm m$^{-2}$ d$^{-1}$ 1000-3500 (Data collected in Moran et al., 2003) | 8 hour collection 33 <br> 24 hour collection 100 | 8 hour collection 167 <br> 24 hour collection 500 |
| Based on Station M 4000m, Measured Range in dpm m$^{-2}$ d$^{-1}$ ~100-1200 (Shaw et al., 1998) | 8 hour collection 3.3 <br> 24 hour collection 10 | 8 hour collection 16.7 <br> 24 hour collection 50 |

FIG. 1

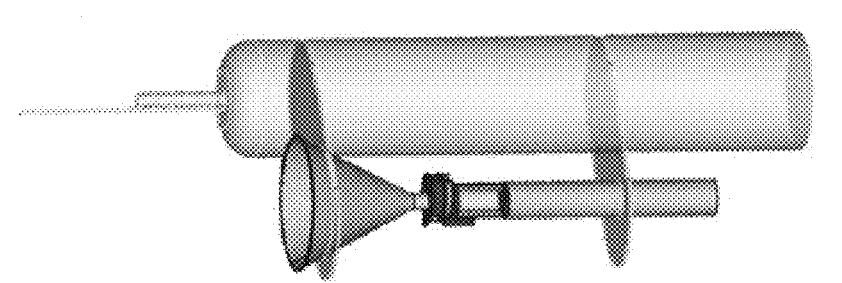
FIG. 3(c)
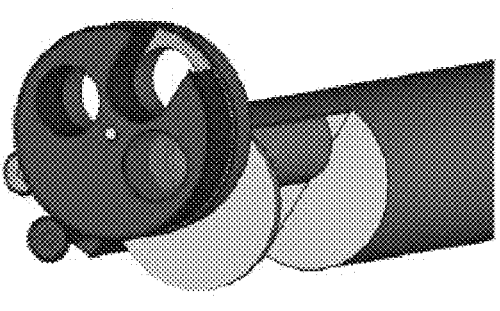
FIG. 3(b)
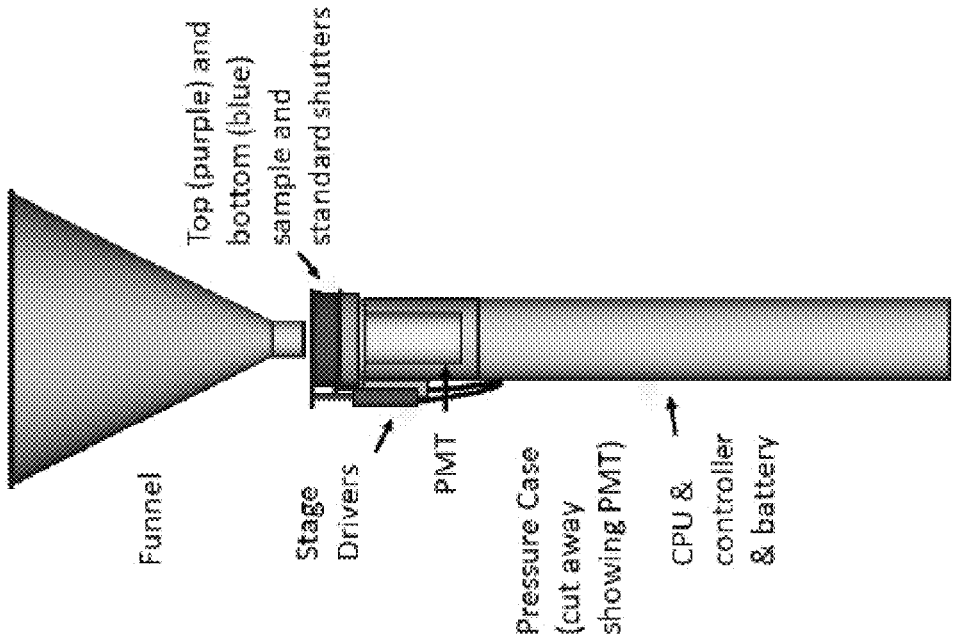
Top (purple) and bottom (blue) sample and standard shutters
Funnel
Stage Drivers
PMT
Pressure Case (cut away showing PMT)
CPU & controller & battery
FIG. 3(a)

IN-SITU BETA-PARTICLE DETECTOR FOR HIGH RESOLUTION 234TH EXPORT MEASUREMENTS

PRIORITY CLAIM

The present application claims the benefit of priority of U.S. Provisional Patent Application No. 63/504,833, titled In-Situ Beta-Particle Detector For High Resolution $^{234}$Th Export Measurements, filed May 30, 2023, and which is fully incorporated herein by reference for all purposes.

BACKGROUND OF THE PRESENTLY DISCLOSED SUBJECT MATTER

Presently disclosed subject matter generally relates to high resolution beta-particle detectors, and more particularly to development of in-situ beta-particle detectors for high resolution $^{234}$Th (Thorium-234) export based mass flux measurements on moored and autonomous sediment traps, such as comprising instruments used in oceanography and limnology to measure the quantity of sinking particulate material in aquatic systems, primarily oceans. In some presently disclosed embodiments, a sea going instrument may be used to measure the $^{234}$Th activity on settling particles in the ocean as an indicator of carbon sequestration as export from the surface ocean.

It is believed there are currently no available technologies that can measure $^{234}$Th on sedimenting particulates in-situ in the ocean water column at activities relevant to ongoing climate change research.

Global estimates of the transport of phytodetritus to the deep ocean as Particulate Organic Carbon (POC) flux put an upper limit of the impact of the "Carbon Pump" to the deep ocean on the order of 5-15% of global carbon export (Laws et al., 2000; Giering et al., 2014). However, changing climate conditions have led to increased intensity and variability of factors that mediate POC flux, particularly in dynamic coastal systems (Smith et al., 2013; 2018). The resultant episodic productivity events associated with transient physical processes are becoming more significant in their contribution to the net transfer of organic carbon from the upper ocean to abyssal depths (Henson et al., 2019; Smith et al., 2013; 2018, Stukel et al., 2017). Ephemeral oceanographic processes like upwelling events, fronts, eddies and filaments lead to productivity events that export particulate carbon out of surface waters as pulses of highly variable duration (Smith et al., 2018; Bishop et al., 2016).

An important factor affecting the efficiency of carbon export to the deep ocean during these events is the particle transit time (Shaw et al., 2019; Smith et al., 2018). The physical dynamics of these systems can enhance both primary production as well as vertical transport of particulate phases by processes such as direct subduction of particles and enhanced aggregation.

The organic material carried with rapidly sinking particles is less susceptible to carbon flux attenuation at mid depths and results in observed periods of high carbon-export efficiency to the abyss (Baldwin et al., 1998; Shaw et al., 1998; Buesseler 1998, Riley et al, 2012; Smith et al., 2018). For example, Buesseler and Boyd (2009) found lower attenuation of surface carbon export through the "twilight zone" following diatom bloom events in a mesotrophic location (K2) compared to an oligotrophic site (Aloha).

Current methods for estimation of carbon attenuation (e.g. Martin fit versus remineralization length scale) have relatively low sensitivity for short timescale events and are susceptible to location bias (Buesseler and Boyd 2009; de Melo Viríssimo et al., 2022). Remineralization with depth is a key term in global biogeochemical models, and spatiotemporal changes in this term have been shown in model experiments to alter the accumulation of atmospheric $CO_2$ (Kwon et al. 2009). A number of critical factors that affect sinking velocity, and hence carbon flux attenuation, are magnified in association with short timescale physical processes in surface waters (Alldredge et al., 1995; Passow and de la Rocha, 2006; Armstrong et al., 2009). Factors such as aggregation of POC phases and ballasting by biogenic and/or lithogenic phases are consistent with observed episodic flux events (Baldwin et al., 1998; Shaw et al., 1998; Buesseler et al., 1998). These important but ephemeral depositions to the abyss have been shown to occur seasonally and inter-annually over periods of days or weeks at magnitudes equal to or greater than monthly or even annual fluxes at other times. The temporal relationship between dynamic surface processes and their contribution to the net POC flux at abyssal depths requires sampling resolution on timescales of hours to days (Bishop et al., 2016; Stukel et al., 2017; Smith et al., 2018).

Carbon Flux Proxy Measurements: Shipboard based depth integrated particle export and remineralization for POC, PIC, nutrient and biogenic phases are often measured using the $^{234}$Th/$^{238}$U disequilibrium method (Rutgers van der Loeff et al., 2006; Waples et al., 2003, Buesseler and Boyd 2009). This approach requires a depth profile of $^{234}$Th and $^{238}$U activities coupled with particulate phase analyte to $^{234}$Th ratios (e.g. POC/$^{234}$Th, PIC/$^{234}$Th, Nut/$^{234}$Th) from one or more depths. In open ocean systems, the timescales of processes that alter carbon export are long with respect to the half-life of $^{234}$Th and the systems can be treated as steady state. In systems where carbon export is perturbed by a short timescale process, a non-steady state approach is necessary (e.g. after Savoye et al. 2006; Resplandy et al. 2012; Buesseler et al., 2020).

As climate change increases the frequency and intensity of short timescale processes, the steady state assumption for carbon export may not be valid and repeated sampling of $^{234}$Th and $^{238}$U profiles is necessary (Savoye et al., 2006). In dynamic systems where a significant fraction of primary productivity results from processes such as upwelling events and eddies that occur on short timescales (Chenillat et al., 2015), the sampling frequency necessary to capture these important events requires intensive ship operations (Buesseler et al., 2020).

As an alternative to ship time intensive efforts, high resolution in-situ systems like the upper water column Carbon Flux Explorer (CFE, Bishop 2009) and the deep ocean Sediment Event Sensor (SES McGill et al. 2016) have been developed. Systems like this show great promise in the effort to translate remote sensing-based estimates of atmospheric carbon uptake in the surface ocean to carbon export to the abyss as carbon attenuation (Bishop et al., 2016; Smith et al., 2018; Shaw et al., 2020). The presently disclosed subject matter describes the development of an in-situ instrument to measure mass flux, as $^{234}$Th export, to complement the types of high-resolution sensors cited above.

SUMMARY OF THE PRESENTLY DISCLOSED SUBJECT MATTER

Aspects and advantages of the presently disclosed subject matter will be set forth in part in the following description, or may be apparent from the description, or may be learned through practice of the presently disclosed subject matter.

Broadly speaking, the presently disclosed subject matter relates to a presently disclosed sea going instrument which is used to measure the $^{234}$Th activity on settling particles in the ocean as an indicator of carbon sequestration as export from the surface ocean.

Still further, presently disclosed subject matter in part may relate to improvement in the state of the art for sensors.

The market for presently disclosed technology (to enable real time monitoring of particle settling in the ocean as mass flux) is based on the thousands of Argos buoyancy engines housing in-situ sensors presently deployed in the oceans to monitor a variety of properties. The presently disclosed technology could be part of the sensor packet on Argos floats to measure mass flux from the surface oceans around the globe. It could also be used on long term moored sediment trap systems.

The presently disclosed technology could support a global network of sensors designed to map factors critical to the evaluation of the impacts of climate change. The specific data generated by this instrument could be critical to the quantification and mapping of carbon sequestration as carbon dioxide transfer from the atmosphere as biogenic material and ultimate burial in the deep ocean. Current methods for measuring $^{234}$Th based mass and carbon flux require extensive use of research vessels and many work hours of research effort. As an add on sensor to in-situ sensor packages, the costs per measurement would fall dramatically.

As a further example, the presently disclosed technology can be adapted to multiple sampling platforms with the goal of providing high temporal resolution $^{234}$Th flux measurements at multiple locations and depths in the ocean. This proxy of mass flux will complement other in situ sensors to provide high resolution data for features such as Chla, accessory pigments, and PIC normalized to mass flux. Chlorophyll-a concentration (Chla) is recognized as an essential climate variable and is one of the primary parameters of ocean-color satellite products.

Thus, the presently disclosed subject matter has the potential for significant impact in the field of sensors.

One presently disclosed exemplary embodiment relates to a method for in-situ high resolution beta-particle detection for measurements of $^{234}$Th activity on settling particles in the ocean as an indicator of carbon sequestration as export from the surface ocean to the ocean floor. Such method preferably comprises using a scintillation material sensor to sense the beta decay activity occurring at a sensor placed in a location of the ocean to be assessed and to output responsive beta energy signals from the sensor, and detecting the presence of $^{234}$Th by discriminating relatively higher beta energy signals from the sensor indicating a measurement of the beta decay of an excited state of its daughter $^{234m}$Pa.

It is to be understood from the complete disclosure herewith that the presently disclosed subject matter equally relates to both method and corresponding and related apparatus and/or systems.

One presently disclosed exemplary system preferably relates to a measurement system for in-situ high resolution beta-particle detection for measurements of $^{234}$Th activity on settling particles in the ocean as an indicator of carbon sequestration as export from the surface ocean to the ocean floor. Such system preferably comprises a scintillation material sensor to sense the beta decay activity occurring at a sensor placed in a location of the ocean to be assessed and to output responsive beta energy signals from the sensor; and a photon signal detector, comprising one of a photomultiplier tube (PMT) or a silicon photomultiplier (SiPM), receiving the responsive beta energy signals, for detecting the presence of $^{234}$Th by discriminating relatively higher beta energy signals from the sensor indicating a measurement of the beta decay of an excited state of its daughter $^{234m}$Pa.

Other example aspects of the present disclosure are directed to systems, apparatus, tangible, non-transitory computer-readable media, user interfaces, memory devices, and electronic smart devices or the like. To implement methodology and technology herewith, one or more processors may be provided, programmed to perform the steps and functions as called for by the presently disclosed subject matter, as will be understood by those of ordinary skill in the art.

Additional objects and advantages of the presently disclosed subject matter are set forth in, or will be apparent to, those of ordinary skill in the art from the detailed description herein. Also, it should be further appreciated that modifications and variations to the specifically illustrated, referred and discussed features, elements, and steps hereof may be practiced in various embodiments, uses, and practices of the presently disclosed subject matter without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the presently disclosed subject matter may include various combinations or configurations of presently disclosed features, steps, or elements, or their equivalents (including combinations of features, parts, or steps or configurations thereof not expressly shown in the Figures or stated in the detailed description of such Figures). Additional embodiments of the presently disclosed subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification, and will appreciate that the presently disclosed subject matter applies equally to corresponding methodologies as associated with practice of any of the present exemplary devices, and vice versa.

BRIEF DESCRIPTION OF THE FIGURES

A full and enabling disclosure of the presently disclosed subject matter, including the best mode thereof, directed to one of ordinary skill in the art, is set forth in the specification, which makes reference to the appended Figures, in which:

FIG. 1 illustrates a Table of exemplary data from practice of the presently disclosed technology, and providing calculated disintegrations per minute (dpm);

FIG. 3($a$) illustrates a conceptual design for an exemplary embodiment of the presently disclosed instrument (sensor);

FIG. 3($b$) illustrates a side view of the sample collection shutters of the exemplary embodiment of FIG. 3($a$); and FIG. 3(c) illustrates a mockup of the exemplary embodiment of the presently disclosed instrument (sensor) of FIG. 3(a) on an Argo float.

Figure 2:
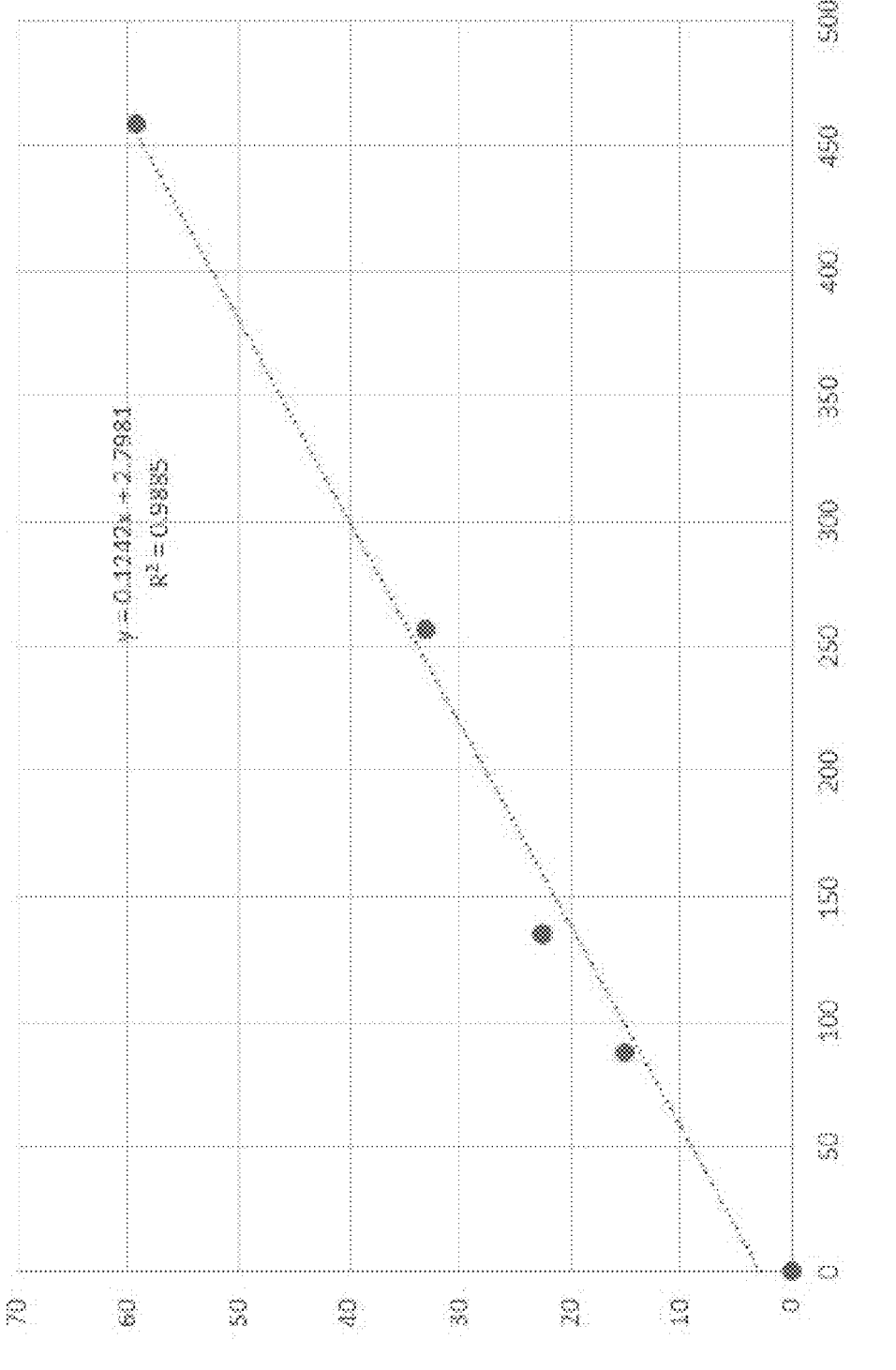
FIG. 2 graphically illustrates preliminary results for a prototype of the presently disclosed instrument lab measured without shielding at sea level, compared to a Germanium Well Gamma measurement.

Repeat use of reference characters in the present specification and drawings is intended to represent the same or analogous features or elements or steps of the presently disclosed subject matter.

DETAILED DESCRIPTION OF THE PRESENTLY DISCLOSED SUBJECT MATTER

It is to be understood by one of ordinary skill in the art that the present disclosure is a description of exemplary embodiments only and is not intended as limiting the broader aspects of the disclosed subject matter. Each example is provided by way of explanation of the presently disclosed subject matter, not limitation of the presently disclosed subject matter. In fact, it will be apparent to those skilled in the art that various modifications and variations can be made in the presently disclosed subject matter without departing from the scope or spirit of the presently disclosed subject matter. For instance, features illustrated or described as part of one embodiment can be used with another embodiment to yield a still further embodiment. Thus, it is intended that the presently disclosed subject matter covers such modifications and variations as come within the scope of the appended claims and their equivalents.

The present disclosure is generally directed to improvements in sensors and related technology, particularly to development of in-situ beta-particle detectors for high resolution $^{234}$Th export measurements on moored and autonomous sediment traps. Such sediment traps may comprise such as instruments used in oceanography, for measuring the quantity of sinking particulate organic material in marine systems. Examples of such systems would broadly encompass a variety of types, including for example oceans and inland saline water bodies.

One example of a presently disclosed device is an in-situ sensor system for the measurement of $^{234}$Th export for deployment under a range of ocean conditions. The activity of $^{234}$Th can be measured via the decay of an excited state of its short-lived daughter $^{234m}$Pa (half-life 1.17 minutes). Approximately 98% of $^{234}$Th decays produce the excited state of 234 Pa called $^{234m}$Pa that provides the signal to be measured. The $^{234m}$Pa decays to the ground state, $^{234}$U. Beta decay produces a spectrum of energies with $^{234m}$Pa strongly skewed toward the upper energy range, with nearly all of these decays having a beta energy of 2.27 MeV (Chu et al., 1999). Such an exemplary device can be based on photon detection from a beta-sensitive plastic scintillator material. The 2.27 MeV beta emission from $^{234m}$Pa is much higher energy than the beta emission for the $^{234}$Th parent (~0.1-0.2 MeV from Chu et al., 1999). Preliminary data indicates that $^{234m}$Pa yields scintillations that can be detected and discriminated from background by their energy distribution, even under high background conditions at sea level (see preliminary results below). A multichannel pulse height analyzer can effectively replace high mass shielding by allowing the differentiation of the photon energies associated with the $^{234}$Th daughter and those from ambient background. The presently disclosed instrument has four critical components: The scintillation material; the scintillation detector; the background evaluation/correction system; and the standard/sample shuttle system.

Such an exemplary instrument can detect the $^{234}$Th activity in sedimenting material as scintillations generated by beta particles ejected during the decay of $^{234m}$Pa, a short-lived daughter isotope of $^{234}$Th. In order to quantify the $^{234}$Th activity, scintillations generated by the beta particles of interest must be identified as different from background beta sources. Several companies make scintillation plastics that are responsive to beta particles in the energy range of our analyte (2.27 MeV for 234 Pa). Our initial studies used scintillator material EJ-204 (Eljen Technology, Texas) in a planar configuration, although other beta-sensitive scintillators and configurations could also work. Plastic scintillation material is attractive because it can be machined or cast into varying shapes to optimize geometries for beta collection. For example, EJ-200 can be obtained as a casting resin and has a photon response similar to EJ-204. Our initial studies evaluated several thicknesses for the material and found significant intensity variations as a function of thickness and geometry with respect to the sample holder. The system was optimized for a 1 mm thick scintillator sheet with an efficiency of 12% (see the table of FIG. 1).

The detector used for our initial proof of concept instrument is an off the shelf, ORTEC photomultiplier tube (PMT) and base placed directly under the scintillator and sample. However, detectors for an in-situ system can be further optimized for size, sensitivity and power consumption. The two main detector types used for scintillation measurements are photomultiplier tubes (PMTs) and silicon photomultipliers (SiPMs). PMTs are electron amplifiers starting with a low-work-function photocathode and passing through 10-12 or more stages of electron acceleration and secondary electron emission. Each detected photon results in a single electron emitted from the photocathode and 105-109 electron gain before reaching the anode. PMTs suited to use with scintillators have relatively low dark current when operated at room temperature, high gain, fast (e.g., ns) and uniform response, and are coupled to fast preamplifiers. The output of these preamplifiers in some embodiments can be directed to a comparator and pulse counter or can be directed to a multichannel analyzer to count pulses while retaining information about their pulse height. PMTs are typically somewhat more expensive than SiPMs, but their larger areas make them more suited to the area detection needed for scintillations. This type of detector would be appropriate for the dedicated bottom mount instrument.

The most critical component of this system is the background evaluation and correction system that, together with atmospheric muon attenuation provided by the water column, will take the place of the mass of Pb shielding normally used to make these types of measurements on board a ship and/or in the laboratory. Atmospheric muons are generated from the interaction of cosmic rays with the atmosphere, and their interaction with matter to produce beta particles with a range of energies is the most variable source of background. These muons can penetrate through several kilometers of ocean water column, but only the most energetic penetrate beyond 10 meters in depth (Tanaka 2020). Atmospheric muon production can vary on short timescales as a function of atmospheric temperature and pressure. For our "proof of concept" instrument, the photons generated by the selected scintillation material were binned by energy and the background spectra were evaluated against that generated by a suite of standards (see FIG. 2). The energy range with the best signal to background spectra was selected manually for the analysis. A high and low pass filter system was applied to the signal to yield the results in FIG. 2. While the lower energy spectrum of these muons will be attenuated with depth in the ocean, it will be necessary to evaluate this and all other sources of ambient background and select the optimum filter parameters automatically at regular intervals during operation. The implementation of this "learning" filter system will be discussed in greater detail later in the presently disclosed subject matter.

For laboratory testing, the analog output of the PMT (or SiPM) can be directed to a multichannel analyzer (MCA) to produce a histogram of counts for different pulse heights. Some manufacturers provide PMT bases that include these MCAs, and often they include proprietary software to communicate between a laboratory computer and the MCA. One exemplary embodiment is to use a Red Pitaya STEMlab 125-14 board to perform this task. The STEMlab 125-14 board includes two RF analog to digital inputs operating at 125 MS/s with 14 bits of resolution.

These boards are designed with Xilinx field-programmable gate array (FPGA) technology that allows them to be reconfigured to serve as different types of instruments. Although the hardware for these boards is not open-source, the software and development system are, and there already exists a distribution on GitHub for converting the board into a 2-channel MCA. We have downloaded and tested this software in our laboratory with the conventional scintillator/PMT system, developed an electronic circuit to simulate beta particle detection events, and shown we have nearly unit efficiency at detecting these pulses. The power consumption of these boards operating as MCAs was found to be 5 W. Although this is a relatively low power consumption, we can use the knowledge gained from laboratory analysis to build a data system for the PMT/SiPM detectors that operates with a fraction of this power in the field and that doesn't require the Red Pitaya board to be active at all times.

In a laboratory testing embodiment, the STEMlab 125-14 can perform the high speed task of collecting and sorting all the pulses observed from a PMT or SiPM (with an appropriate change of time scale and selection of appropriate input gain). The readout of the histograms and interpretation of pulse height data can be done rapidly on a desktop computer for the purpose of selecting the threshold for or range of pulse heights that best differentiate our target analyte(s) from background. After applied voltage and threshold levels are determined, a data analysis system may be constructed using one or more comparator circuits that apply critical thresholds for pulse counting, enabling a very low power pulse counter that has optimal selectivity for our analyte.

The final component of the system for exemplary embodiments is the shuttle system for moving the sample and standards with respect to a fixed photon detector that will be housed in a pressure case. A simple rack and pinion configuration is one example embodiment. Per such exemplary embodiment, a stepper motor coupled to pinioned circular bottom shutter is used to collect samples for counting; move the samples from the detector stage to allow for standard measurement, background measurement and collection surface cleaning. A similar upper "shutter" can be configured to move a standard in position above the detector for calibration and optimization of signal to background (see FIGS. 3(a), 3(b), and 3(c)). In exemplary embodiments, once the components are optimized to measure the betas of interest, the assembled system can be tested and evaluated for further optimization.

Rationale for instrument development. Evaluation of the factors that affect the attenuation of carbon transfer from the upper ocean to the deep sea are critical in predicting changes in global carbon budgets with changing climatic conditions. One critical factor is the rate of particulate transfer from the surface ocean to abyssal depths, as mass flux. Methods for the measurement of carbon transfer efficiency between surface and deep waters in dynamic open ocean and coastal systems require high resolution to capture major export events (Buesseler et al., 2008; Bishop et al., 2016; Stukel et al., 2017; Smith et al., 2018; Buesseler et al., 2020). Variations in climatic and upper ocean conditions are linearly linked to carbon cycling and ultimate burial in deep sea sediment. As these processes become more variable and extreme with changing climate conditions, high-resolution measures of their impact on carbon export are necessary. The $^{234}$Th/$^{238}$U disequilibrium approach to estimation of the export of $^{234}$Th is currently an important proxy for estimating organic carbon export from the upper ocean. However, dynamic conditions typical of high flux regions do not allow steady state conditions with respect to maintenance of a constant $^{234}$Th inventory, precluding reliable results for single profile site evaluation. Thus, in dynamic systems, the $^{234}$Th/$^{238}$U disequilibrium approach is ship time intensive, and results in limited spatial and temporal resolution of changes in particle settling time and carbon remineralization. The evaluation of remineralization rates with depth, as carbon flux attenuation, is a key term in global biogeochemical models. It is therefore very likely to be a key global warming feedback mechanism.

The instrument exemplary embodiment disclosed here supports autonomous monitoring of mass flux, as $^{234}$Th export, and could return high resolution data elucidating the frequency, intensity and duration of export fluxes and remineralization of particulate matter at multiple depths. The high-resolution sampling from autonomous platforms (e.g., moored and Lagrangian sediment traps (LST), and moored sediment analyzers, (SES)), coupled with in-situ measurement of carbon proxies (e.g. fluorescence) enables an unprecedented ability to temporally link high resolution remote sensing products to high resolution deep sea moored and autonomous sensing platforms. The development of this instrument provides the capacity to collect data and knowledge necessary for updates of biogeochemical flux models like those used by regional to global stakeholders like the Intergovernmental Panel on Climate Change.

Preliminary Results

Sensitivity and Resolution for the Presently Disclosed System

One primary value of the presently disclosed device is to increase the resolution for the measurement of mass flux through the water column via the proxy $^{234}$Th using both autonomous and moored sediment traps. The limit for sampling resolution is a function of the efficiency of our detector system, the capacity to resolve the ambient background and the sediment trap opening (as particle collection area). The two sample collection modes considered here are an autonomous sediment trap such as an LST or ARGO float with a small collection area (e.g. ~0.10 $m^2$ after Sherman et al., 2011) and a moored system like the SES (e.g. ~0.50 $m^2$ after McGill et al., 2016). The current "proof of concept" instrument using a planar scintillator with no shielding has an efficiency of >10% above background (see FIG. 2). This geometry reflects a worst-case scenario.

Based on our current system, it is possible to measure the minimum detectable activity of a sample for different possible background counts. The background for the laboratory prototype for the selected energy range is ~150 counts per minute (cpm). This means that the purpose of determining a detection limit as a function of counting time (resolution), the counts are sufficient to approach a Gaussian distribution (Blue et al., 1987).

Based on equation 1 (below) adapted from Blue et al., (1987), for a background of 150 cpm and a measurement of 8 hours duration the minimum detectable analyte counts above background would be 1.3 cpm for an a of 0.05 (95% confidence). Based on a conservative counter efficiency of 10%, the minimum detectable sample activity would be 13 dpm. For comparison, if the background in-situ is primarily associated with $^{40}$K (estimated at ~12 dpm in an exemplary sample volume) and the muon contribution is of similar magnitude (25 cpm tot), the minimum detectable activity for a sample would be 5 dpm.

$$cpm_{min} = \frac{z^2 + z\sqrt{8N_b t + z^2}}{2t} \qquad \text{eq. 1}$$

Where: $cpm_{min}$ is the minimum total analyte counts (in the presence of background) that can be detected per minute, No is the total background counts per minute, z is the number of standard deviations that we want the signal and background separated (from Blue et al., 1987), and t is the sampling time in minutes.

The minimum detectable decays per minute ($dpm_{min}$) is given by the $cpm_{min}$ divided by the detector efficiency (10% in this case), per Eq. 2:

$$dpm_{min} = \frac{cpm_{min}}{0.10} \qquad \text{eq. 2}$$

The table of FIG. 1 provides calculated $dpm_{min}$ with the presently disclosed system at sea level background levels and at an expected maximum background at depths below 100 meters. These are converted to dpm m$^{-2}$ d$^{-1}$ for an 8 hour collection for a large trap configuration (as an SES 0.5 m$^2$) and an autonomous trap (as an LST 0.1 m$^2$). Even under worst case conditions, the range of measured $^{234}$Th export exceeds the minimum detectable dpm for the prototype system.

Based on the calculations above and the comparison to field measurements, the current prototype detects $^{234}$Th fluxes at the low end of the measured range for both small and large trap configurations at high resolution (short sampling windows).

FIG. 2 graphically represents preliminary results for the prototype (presently disclosed) instrument measured without shielding at sea level in our laboratory compared to a Germanium Well Gamma measurement.

Additional Aspects

The following additional aspects may be evaluated based on instrument design, evaluation and demonstration described below.

Scintillation Materials and Sensitivity for Beta Counting:

Depending on application, the proposed instrument will utilize a variety of solid scintillation materials that are now available that show specificity for the detection of beta particles in the energy range consistent with the decay of $^{234}$Th and its short-lived daughter $^{234m}$Pa. At the earth's surface, cosmic radiation interacts with ambient molecules (including detector materials) to generate significant background for any beta measurements and requires significant shielding and/or very selective background correction. The attenuation of these high energy particles with depth in the ocean reduces the need for shielding for in-situ measurement (Formaggio and Martoff, 2004; C. J. Martoff pers. Comm.). Thus, the preliminary results presented above reflect a worst-case condition with respect to muon generated background. The most significant source of ambient radionuclide background beta emissions in the ocean is the decay of $^{40}$K which emits a beta particle of 1.45 MeV with ~80% probability. While 40K is ubiquitous, the background for small sample volumes is minimal (<5 dpm for a 4 cm diameter×1 cm deep sample cell, see presently disclosed design section below) due to the short penetration distance of the beta emissions and low overall 40K activity.

The interaction of individual beta particles with plastic scintillator material yields a packet of photons whose intensity (as number) is proportional to the lifetime of the interaction. Thus, because beta attenuation in any material is a function of energy, the intensity of the photon pulse is proportional to the energy of the beta. This energy distribution allowed the selection of an energy "window" where the beta signals of interest could be differentiated from ambient background in an unshielded system at sea level (see results discussed herein). The sources of background that can contribute to background within the water column are environmental radioactivity (e.g., U and Th decay series from lithogenic material, $^{40}$K decay), impurities in apparatus (mostly the same nuclides), and the showers of elementary particles produced by interaction of cosmic rays with the Earth's atmosphere (Heusser, 1995). Preliminary results suggest that photon energy spectrum data collected in-situ can be used to select an appropriate energy "window" for sampling locations and depths in the ocean.

Two different exemplary embodiment of systems can be based on different detector types (PMT and geometries (see discussion of H2 below). Both exemplary systems have the capacity to be isolated from surrounding seawater by a shutter system (see discussion of H5 below) to reduce the $^{40}$K contribution to the background. The sample can be collected in an exemplary trap with a specially designed shutter cup with a depth of ~3 cm to account for the flocculant nature of the sample, but well within the penetration depth of the 2.27 MeV beta particles generated by the $^{234m}$Pa target analyte. The diameter of the exemplary cup can be ~4 cm yielding a volume of ~12 mL. The exemplary low volume cup will ensure that any contribution of the $^{40}$K beta particles is very low with respect to the $^{234m}$Pa signal.

Detector Selection:

Depending on application, one of two detector types will be used for scintillation measurements, photomultiplier tubes (PMTs) and silicon photomultipliers (SiPMs). PMTs are electron amplifiers starting with a low work-function photocathode and passing through 10-12 or more stages of electron acceleration and secondary electron emission. Each detected photon results in a single electron emitted from the photocathode and $10^5$-$10^9$ electron gain before reaching the anode. PMTs suited to use with scintillators have relatively low dark current when operated at room temperature, high gain, fast (e.g., ns) and uniform response, and are coupled to fast preamplifiers. The output of these preamplifiers in some embodiments may be directed to a comparator and pulse counter or can be directed to a multichannel analyzer to count pulses while retaining information about their strength. PMTs are typically somewhat more expensive than SiPMs, but their larger areas make them more suited to the area detection needed for scintillations. This type of detector would be appropriate for the dedicated bottom mount instrument.

SiPMs are a variation of avalanche photodiodes (APDs) operated in Geiger mode. The elements of a SiPM store charge and experience a breakdown when a photon is absorbed to create a conductive channel. This leads to many electrons passing through the element before the current flow shuts down. These detectors are often produced in the form of many individual pixels that are operated as a unit rather than as individual detection elements. These typically have smaller areas than PMTs and also respond more slowly but are insensitive to magnetic fields. SiPMs are common choices for handheld or portable applications and will be evaluated in conjunction with light guide materials to allow versatility in detector/funnel orientation.

Both PMTs and SiPMs require high operating voltages, with PMTs requiring ~1000 VDC and SiPMs requiring ~200 VDC. In each case, there exist high voltage power units that upconvert low DC voltages efficiently. Exemplary embodiments for testing may include one PMT type and one SiPM type made by Hamamatsu for our scintillator application. The specific exemplary PMT for one such embodiment is the Hamamatsu C139530-01 scintillation probe, which operates on ±5 VDC with nominally 100 mA of current (0.5 W power consumption). This unit has a relatively small (for a PMT) circular active area with a diameter of 12 mm. Although this unit comes with a thin (0.5 mm) built-in plastic scintillator material and the detection circuit provides a comparator and 5 V output pulses, in some presently disclosed embodiments, we can replace the scintillator with our own somewhat thicker plastic scintillator and modify the circuitry to provide an analog output for multichannel analysis.

Real Time Particle Detection with Background Correction:

The scintillation detection system will be optimized to distinguish "counts" due to analyte decay from background counts as a function of ambient background as a function of measurement location (i.e. depth in the water column). The energy and penetration depth of 40K beta decay products are lower than those of the analyte, so the relative attenuation of the $^{234m}$Pa and the $^{40}$K betas in the scintillator should provide a discernable difference in photon pulse intensity that can be mitigated with the presently disclosed energy discriminator. Residual high energy muons have very great penetration depths and their average energy and number density will vary with submerged depth. For some presently disclosed embodiments, their interaction with the scintillator material will generate betas with higher energies, but their occurrence should diminish with depth in the water column. From a surface intensity of ~$10^{-2}$/cm$^2$-s, muon flux falls to about $10^{-4}$/cm$^2$-s at a depth of 100 meters (Heusser, 1995). The natural activity of potassium is about 31000 Bq/kg for pure potassium, so at a nominal seawater concentration of ~380 mg/L, a practitioner of presently disclosed subject matter would expect to observe ~12 Bq in a liter of seawater or on the order of 26 DPM for the exemplary cup volume disclosed. This reflects a very low background with respect to the expected sample activity and would produce minimum error once subtracted. Further, the energy discriminator (based on multichannel peak-height analysis) for some presently disclosed embodiments will reduce the potential background from the lower energy $^{40}$K beta particles and the high energy muon produced beta particles. This likely provides a route to distinguish target scintillation counts from background by judicious selection of scintillator thickness combined with one or two thresholding levels for peak counting. A much lower potential background contribution occurs from the small amount of lithogenic material collected based on the short collection times.

Shutter System for Sample Count Collection, Standardization and Background Correction:

The presently disclosed instrument will for some exemplary embodiments make two short duration higher power (5 W) measurements using the multichannel analyzer described above to "train" the energy filter system prior to the longer duration lower power sample measurement. A measurement of background with only ambient seawater in the sample chamber may be compared with a second measurement of ambient seawater and a planchette loaded with a $^{238}$U standard to supply activity of its daughter, $^{234}$Th. These two measurements allow optimization of the signal to background ratio by selection of the optimized "energy" window for that sampling depth so that longer duration measurements at lower power can be recorded.

Following sample accumulation in the sample chamber, the sample counts may be collected for the energy window determined in modes 1 and 2 until a statistically significant total count is collected. Then the standard planchette is again rotated into position above the chamber containing the sample. This allows the evaluation of self-absorption of sample derived beta particles.

FIG. 3(a) is a conceptual design for the overall instrument, FIG. 3(b) is a side view of the sample collection shutters, and FIG. 3(c) is a mockup of the instrument on a Argo float. For example, the two shutters may be rotated to: collect sample; isolate the sample from the funnel for counting; place the standard over the PMT for standard evaluation; and move an empty cell with only ambient seawater over the PMT for background counting. The cutouts allow for flushing the funnel.

Optimization of the Prototype Instrument.

Once a detection system is submerged below 10 meters, the contributions from lower energy muons diminish leaving primarily residual high energy muons (>30 GeV) from atmospheric cosmic ray interactions. There is a depth independent background from $^{40}$K that decays producing a beta particle with an energy of 1.31 MeV that can be minimized for a small volume sample. The resultant measurements at 10 meters depth will represent a "worst case" in-situ scenario as the contribution from high energy muons will diminish with depth in the water column. Tank tests provide an opportunity to complete evaluation of each instrument system under simulated ambient conditions.

The subject matter outlined above for some embodiments results in instrumentation that can be adapted to multiple sampling platforms with the goal of providing high temporal resolution $^{234}$Th flux measurements at multiple depths. This proxy of mass flux complements other in-situ sensors to provide high resolution data for features such as Chlorophyll a, accessory pigments, and PIC normalized to mass flux. These data in turn can be correlated by the user to the frequency and magnitude of surface ocean features that drive specific episodic flux thresholds. The long-term application of the presently disclosed instrumentation enables identification of specific driver(s) of changes in carbon export and attenuation over time, testable improved methods of POC quantification through proxy ratios to mass flux, and confirmation of mechanistic underpinning to how variation in surface features translates to efficiency of carbon export to the abyss. This presently disclosed instrumentation supports analysis of an extraordinary range of factors to be systematically considered including when and how episodic POC transfers to the abyss relate to specific surface ocean features, temperature, export flux, ballasting, the abundance and size distribution of fast and slow sinking particles.

Global warming is now a well-documented phenomenon that is influencing every aspect of the world, from increased storm intensity to melting of polar ice sheets and rising sea level. Understanding the impact of such changes on climate and on drivers of surface ocean productivity and carbon export will require high resolution process studies. In-situ sensors will be critical components of these necessary future process studies. The presently disclosed subject matter will help validate models of carbon export from the surface ocean, including rapid episodic fluxes, remineralization at abyssal depths and sequestration on the sea floor.

Variations on this sensor not described here could be suited to other analytes, including some targeted at laboratory or commercial uses (e.g., Radon, potassium, 14C, etc.).

This written description uses examples to disclose the presently disclosed subject matter, including the best mode, and also to enable any person skilled in the art to practice the presently disclosed subject matter, including making and using any devices or systems and performing any incorporated methods. The patentable scope of the presently disclosed subject matter is defined by the claims, and may include other examples that occur to those skilled in the art. Such other examples are intended to be within the scope of the claims if they include structural and/or step elements that do not differ from the literal language of the claims, or if they include equivalent structural and/or elements with insubstantial differences from the literal languages of the claims.

What is claimed is:

1. A method for in-situ high resolution beta-particle detection for measurements of $^{234}$Th activity on settling particles in the ocean as an indicator of carbon sequestration as export from the surface ocean to the ocean floor, comprising:

using a scintillation material sensor to sense the beta decay activity occurring at a sensor placed in a location of the ocean to be assessed and to output responsive beta energy signals from the sensor, and detecting the presence of $^{234}$Th by discriminating relatively higher beta energy signals from the sensor indicating a measurement of the beta decay of an excited state of its daughter $^{234m}$Pa.

2. The method according to claim 1, wherein the relatively higher beta energy signals comprise about 2.27 MeV beta emissions.

3. The method according to claim 1, wherein:

the beta energy signals are detected as scintillation generated photon signals; and detecting and discriminating includes using signal pulse height analysis of a spectrum of beta energy signals generated by the scintillation material, for differentiation of photon energies associated with the $^{234}$Th daughter from those comprising ambient background.

4. The method according to claim 3, further comprising using a multichannel pulse height analyzer in place of high mass shielding.

5. The method according to claim 1, wherein the scintillation materials comprise beta-sensitive plastic scintillation materials that are responsive to beta particles in the energy range of about 2.27 MeV.

6. The method according to claim 5, wherein the plastic scintillation materials a planar scintillator comprising a sheet from 1 mm to several cm thick and with an efficiency of at least 10% above the ambient background.

7. The method according to claim 6, wherein the plastic scintillation materials include a polymer base comprising polyvinyl toluene.

8. The method according to claim 1, wherein detecting and discriminating includes using a photon signal detector, with the detector comprising one of a photomultiplier tube (PMT) or a silicon photomultiplier (SiPM).

9. The method according to claim 8, wherein detecting and discriminating includes using a photon signal detector comprising a photomultiplier tube (PMT) placed directly under the plastic scintillation materials and a sample to be assessed.

10. The method according to claim 9, wherein the output of the PMT is coupled to a fast preamplifier, with the output of the preamplifier directed to one of: (a) a comparator and pulse counter or (b) to a multichannel analyzer, to count pulses while retaining information about their pulse height.

11. The method according to claim 10, further comprising producing a histogram of counts for different pulse heights.

12. The method according to claim 10, further comprising collecting and sorting all the pulses observed from the PMT.

13. The method according to claim 1, further comprising providing a motor-driver shuttle sample system for selectively providing sequential analysis by movement of samples and standards adjacent to the scintillation material sensor.

14. The method according to claim 13, further comprising selectively performing sequential analysis of ambient background counts, sample and background counts, standard counts with ambient background and standard counts over the sample counts.

15. The method according to claim 14, wherein the location of the ocean comprises a selected depth from the ocean surface.

16. The method according to claim 1, further comprising using a plurality of the scintillation material sensors to respectively sense the beta decay activity occurring at sensors placed in a corresponding plurality of locations of the ocean to be assessed and to output responsive beta energy signals from the respective sensors.

17. The method according to claim 16, wherein using a plurality of the scintillation material sensors comprises using at least one of autonomous or moored sediment traps.

18. The method according to claim 1, further comprising using a sample collection shutter system associated with an existing floating collection sensor.

19. The method according to claim 18, wherein the sample collection shutter system includes two shutters respectively controlled to rotate to collect a sample, isolate the sample for counting, position a standard over an associated photon signal detector for standard evaluation, and move an empty cell with only ambient seawater over the photon signal detector for background counting.

20. The method according to claim 1, further comprising adapting the method of associate a plurality of scintillation material sensors to multiple sampling platforms, and providing high temporal resolution $^{234}$Th flux measurements recorded at multiple depths in the ocean.

21. The method according to claim 20, further comprising correlating the measurements recorded with the frequency and magnitude of surface ocean features that drive specific episodic flux thresholds.

22. A measurement system for in-situ high resolution beta-particle detection for measurements of $^{234}$Th activity on settling particles in the ocean as an indicator of carbon sequestration as export from the surface ocean to the ocean floor, comprising:

a scintillation material sensor to sense the beta decay activity occurring at a sensor placed in a location of the ocean to be assessed and to output responsive beta energy signals from the sensor; and a photon signal detector, comprising one of a photomultiplier tube (PMT) or a silicon photomultiplier (SiPM), receiving the responsive beta energy signals, for detecting the presence of $^{234}$Th by discriminating relatively higher beta energy signals from the sensor indicating a measurement of the beta decay of an excited state of its daughter $^{234m}$Pa.

23. The measurement system according to claim 22, wherein the relatively higher beta energy signals comprise about 2.27 MeV beta emissions.

24. The measurement system according to claim 22, wherein:

the beta energy signals comprise scintillation generated photon signals; and the measurement system further comprises a multichannel pulse height analyzer for analyzing a spectrum of beta energy signals generated by the scintillation material, for differentiation of photon energies associated with the $^{234}$Th daughter from those comprising ambient background.

25. The measurement system according to claim 22, wherein the scintillation materials comprise beta-sensitive plastic scintillation materials that are responsive to beta particles in the energy range of about 2.27 MeV.

26. The measurement system according to claim 25, wherein the plastic scintillation materials a planar scintillator comprising a sheet about 1 mm thick and with an efficiency of at least 10% above the ambient background.

27. The measurement system according to claim 22, wherein the photon signal detector comprising a photomultiplier tube (PMT) placed directly under the plastic scintillation material sensor and a sample to be assessed.

28. The measurement system according to claim 27, further comprising a motor-driver shuttle sample system for selectively moving samples and standards adjacent the scintillation material sensor.

29. The measurement system according to claim 28, wherein the motor-driver shuttle sample system includes two shutters respectively controlled to rotate to collect a sample, isolate the sample for counting, position a standard over an associated photon signal detector for standard evaluation, and move an empty cell with only ambient seawater over the photon signal detector for background counting.

30. The measurement system according to claim 22, further comprising a plurality of the measurement systems to respectively sense the beta decay activity occurring at sensors placed in a corresponding plurality of locations of the ocean to be assessed.

31. The measurement system according to claim 30, wherein the plurality of measurement systems respectively are associated with one of an autonomous sediment trap or a moored sediment trap.

32. The measurement system according to claim 31, wherein the plurality of measurement systems are respectively associated with a plurality of existing floating collection sensors.

33. The measurement system according to claim 29, wherein the plurality of measurement systems are each configured with a respective motor-driver shuttle sample system for selectively moving samples and standards adjacent its associated scintillation material sensor for recording and providing high temporal resolution $^{234}$Th flux measurements recorded at multiple depths in the ocean.

34. The measurement system according to claim 33, wherein the plurality of measurement systems are each configured for correlating measurements recorded with the frequency and magnitude of surface ocean features that drive specific episodic flux thresholds.

* * * * *